United States Patent [19]

Crenshaw et al.

[11] Patent Number: 5,276,042
[45] Date of Patent: Jan. 4, 1994

[54] TREATMENT OF PREMATURE EJACULATION

[76] Inventors: Roger T. Crenshaw; Mark G. Wiesner, both of 8950 Villa La Jolla, Ste. 2131, La Jolla, Calif. 92037

[21] Appl. No.: 48,844

[22] Filed: Apr. 16, 1993

[51] Int. Cl.$^5$ ............................................ A61K 31/445
[52] U.S. Cl. ........................................................ 514/321
[58] Field of Search ............................................ 514/321

[56] References Cited

U.S. PATENT DOCUMENTS 4,007,196  2/1977  Christensen et al. ............... 546/197
4,721,723  1/1988  Barnes et al. ......................... 514/321

Primary Examiner—Leonard Schenkman
Attorney, Agent, or Firm—Olson & Hierl, Ltd.

[57] ABSTRACT

Premature ejaculation by a male human patient is treated by administration of paroxetine.

7 Claims, No Drawings

TREATMENT OF PREMATURE EJACULATION

TECHNICAL FIELD

This invention relates to the treatment of a sexual dysfunction. More particularly, this invention relates to the treatment of premature ejaculation in a human male patient.

BACKGROUND OF THE INVENTION

Premature ejaculation is a sexual dysfunction that has been variously estimated to effect up to 75 percent of the population (Kinsey et al., 1949, p. 580; Masters and Johnson 1967, 1971 and 1973). Regardless of the figures in the literature and the definition of premature ejaculation, this problem has remained substantially unchanged in the past twenty years regardless of the psychological, biochemical, pharmacological and clinical psychiatric literature. The term "premature ejaculation" includes congenital premature ejaculation as well as primary premature ejaculation where the male ejaculates extremely rapidly, e.g., prior to penetration with coitus or within ten to twenty strokes after intromission, so as to adversely affect the sexual relationship between the involved partners. The psychoanalytical definition of ejaculation, in less than one minute, also suffices for these purposes as well as the Masters and Johnson definition where the male ejaculates 50 percent of the time more rapidly than the female is able to have an orgasm if she has no orgasmic dysfunction of her own. Premature ejaculation by any of the foregoing definitions can be treated by the method of the invention.

Premature ejaculation is a considerable factor in sexual as well as marital discord. It is estimated that this factor is present in at least about 20 percent of clinical cases. However, heretofore an effective, relatively inexpensive treatment that can be administered by any practicing physician without specialized knowledge has not been available.

The use of fluoxetine hydrochloride (Prozac ®) is described in U.S. Pat. No. 5,151,448 to Crenshaw and Wiesner. It has now been found, however, that similar treatment at a relatively lower dose of active ingredient can be achieved by practicing the present invention.

SUMMARY OF THE INVENTION

Premature ejaculation in male human patients can be effectively treated by the administration, preferably oral, of a paroxetine dose effective to delay the onset of ejaculation during subsequent sexual intercourse. One preferred mode of treatment within the purview of the present invention is the chronic administration of paroxetine in an amount in the range of about 3 milligrams to about 30 milligrams per day, preferably about 10 milligrams per day.

Oral administration is the preferred route of administration. Paroxetine is preferably administered as the hydrochloride salt, i.e., as paroxetine hydrochloride.

DETAILED DESCRIPTION OF PREFERRED EMBODIMENT

Paroxetine is a known antidepressant and is commercially available under the trade designation Paxil ® as paroxetine hydrochloride. This compound can be represented by the formula

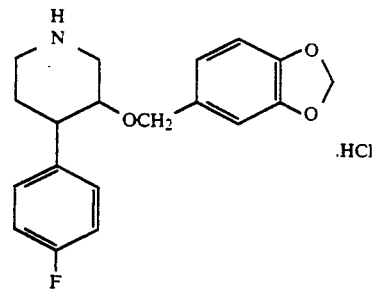

and is also known by its chemical name as trans-(−)-3-(1,3-benzodioxol-5-yloxy)methyl-4-(4-fluorophenyl)-piperidine hydrochloride. The molecular weight of paroxetine is 329.37. The hydrochloride salt is a crystalline solid melting at 118° C.

The synthesis of paroxetine and of the acid addition salts thereof is described, inter alia, in U.S. Pat. No. 4,007,196 to Christensen et al. and U.S. Pat. No. 4,721,723 to Barnes et al.

It has now been found that premature ejaculation in a male human patient suffering from such an affliction can be effectively ameliorated and treated by the administration to the patient of an effective dose of paroxetine either in its free base form or its acid addition salt form. Paroxetine is an amine, and, as is well known, amines readily form acid addition salts with inorganic acids as well as organic acids.

The term "paroxetine," as used herein and in the appended claims, means the free base form as well as an acid addition salt form of trans-(−)-3-[(1,3-benzodioxol-5-yloxy)methyl-4-(4-fluorophenyl)piperidine, anhydrous as well as hydrated. Also included within the purview of this invention is the use of the pharmacologically acceptable salts of the paroxetine base formed with substantially non-toxic acids. Such acid addition salts include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono and dicarboxylates, phenylsubstituted alkanoates, hydroxy alkanoates and alkanedioates, aromatic acids, aliphatic and aromatic sulfonic acids, etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonates, naphthalene-1-sulfonate, naphthalene-2-sulfonate, mandelate and the like salts. While paroxetine is an anti-anxiety drug, it is to be noted that other anti-anxiety drugs such as chlordiazepoxide (Librium ®) and diazepam (Valium ®) are not suitable for the treatment of premature ejaculation.

For the treatment contemplated by the present invention, the preferred route of administration is oral administration; however, other routes of administration, e.g., parenteral, by suppositories, buccal dosage forms, skin patch, and the like, can also be utilized. The active ingredient in the individual dosage forms can be combined with the conventional pharmaceutical excipients and formed into tablets, capsules, and the like. Tablets may be scored for divided dosage administration. Alternatively, the active ingredient may be dissolved in a suitable liquid vehicle such as water, fruit juice, or the like. For chronic administration of the active ingredient oral dosage forms are preferred.

The specific dosage and duration of treatment may vary depending upon the particular patient. However, usually premature ejaculation is successfully treated by administering paroxetine in a daily dose in the range of about 3 milligrams to about 30 milligrams for a time period of at least about 3 months, preferably for a time period of at least about 6 months. In some instances paroxetine is administered chronically as long as the patient remains sexually active. A daily dose of about 10 milligrams is preferred.

The administered dosage can also vary over a period of time. A particularly preferred such treatment regimen contemplates the administration of a daily dose of about 10 milligrams for the first two weeks of treatment, then a daily dose of about 20 milligrams for the next four weeks of treatment, next a daily dose of about 20 to about 60 milligrams for two weeks, followed by a daily maintenance dose of about 20 to about 60 milligrams for an extended time period as required.

The present method of treatment provides at least three major areas of improvement over the old methods for control of premature ejaculation which mainly followed behavioral cognitive methodology and relied upon a model which was threefold: (1) that premature ejaculation was due to prior conditioning and therefore largely in part to the person's rapid masturbatory behavior as an adolescent, (2) that there was some anxiety involved and therefore a release of adrenaline to the neuroreceptors causing a flight/fight/fear mechanism and sympathetic activity increase of the nervous system and (3) that there was an increased muscular tone (increased beta afferent neurological response) which caused the person to ejaculate rapidly due to increased rapidity of all reflexes. In addition, there is a fourth postulate, that is, (4) a biological difference between males exhibiting premature ejaculation and those males without premature ejaculation, which may be borne out in some of the literature describing cortical evoked potentials. See, for example, Andrologia 20(4):326-330 (1988). Using any of these models for purposes of comparison, the present method accomplishes the following: (A) specialized information to treat the person with premature ejaculation is not required, (B) the treatment of premature ejaculation is achieved rapidly with medication available to all physicians.

In addition, the cost of treatment to the patient is reduced at least about six-fold. Such improvements in reduced cost, delivery, and access, as well as the fact that any licensed physician can prescribe this medication, provide a significant advantage over that what was heretofore available to the estimated 23 million male patients in the United States alone who suffer from premature ejaculation but many of whom may not have access to the limited number of qualified therapists. See, for example, *Spector et al., Archives of Sexual Behavior,* 19 (4): 389-408.

The present invention is further illustrated by the following case studies.

CASE ONE

A 49-year-old white male presented with a lifetime history of premature ejaculation. His ejaculation occurred within 30 seconds of penetration and was not changed either by physical position or by partner. At the time that he presented for therapy, he and his wife had been married for 24 years. Although he had been through multiple psychotherapies and tried many other medications, he was unable to control his premature ejaculation beyond the 30-second mark. He was begun on Paxil®, 20 mg. per day, and within two weeks reported that he was able to sustain penetration for 3 to 5 minutes in the male superior position and 4 to 7 minutes in the female superior position. He was taking no other medications at that time and was in physically good health.

CASE TWO

A 42-year-old white male presented with a lifetime history of premature ejaculation. With masturbation he ejaculated within 30 seconds and with all attempts at intercourse he ejaculated within 30 seconds. He oftentimes ejaculated prior to penetration. He was started on Prozac®, 20 mg., approximately six months prior to the initiation of Paxil®. On Prozac® he found that he was at the 60 mg. dosage level and still ejaculating within 30 seconds. He was begun on Paxil®, 20 mg., and was able to last 3 to 5 minutes without any side-effects. He and his wife were able to sustain intercourse in all positions without any difficulty.

CASE THREE

A 55-year-old male presented with premature ejaculation, i.e. ejaculated in less than 30 seconds in all positions, and some degree of impotence. He had been treated with Prozac®, 20 mg., for the premature ejaculation, and although on Prozac® he was able to last approximately 1 minute, at the 40 mg.-dosage level he was noticing that his impotency was becoming worse. He was begun on Paxil®, 20 mg. per day, and there was a complete reversal of all signs and symptoms of impotence. He was able to sustain an erection sufficient for penetration for approximately 5 minutes. His wife was then able to be orgasmic with intercourse. No further interventional therapy was deemed necessary.

CASE FOUR

A 32-year-old male presented with a lifetime history of premature ejaculation. He ejaculated within 10 seconds of intromission. He also noted that he often ejaculated with foreplay prior to penetration. He was begun on Paxil®, 20 mg. per day, but developed ejaculatory inability, i.e., the inability to ejaculate prior to the onset of tiredness, and was reduced to Paxil®, 10 mg. per day. He then was able to ejaculate within approximately 5 minutes of intravaginal thrusting. No further therapy was needed at that time.

CASE FIVE

A 28-year-old black male presented with a lifelong history of premature ejaculation. He was married, and at the point of initial evaluation was taking Prozac®, 20 mg. per day, prescribed by another physician. He was still ejaculating within a fairly short period of time, estimated by him and his wife at less than 1 minute. He was begun on Paxil ®, 20 mg. per day. Within three weeks they both reported that he was lasting 5 minutes or longer with each coital encounter. The patient was followed for three months and during that time period there was no change from the 5-minute period of duration prior to ejaculation.

CASE SIX

A 57-year-old white male presented with a lifetime history of premature ejaculation, i.e., ejaculated in less than 30 seconds in most coital encounters. He also reported a slight difficulty with erections on about 20 percent of coital encounters, as well as oftentimes ejaculating prior to penetration. He was on 40 mg. of Prozac ® due to depression, prescribed to him by another physician. At the time of initial evaluation, he was begun on 20 mg. of Paxil ® and did well sexually. The impotence cleared without difficulty; however, the depression was still present and he was begun on 40 mg. of Paxil ®. On that dosage of Paxil ® he had no difficulty either with erection or with ejaculation. It took him approximately 5 minutes to ejaculate. The premature ejaculation was considered cured, as well as the difficulty with erections.

CASE SEVEN

A 36-year-old male presented with a lifelong history of premature ejaculation. He and his wife arrived at therapy at the point of divorce. He was begun on Paxil ®, 20 mg. per day. Within two weeks he and his wife reported that he was able to last between 3 to 5 minutes in all positions. There were no side-effects. A follow-up in three months was scheduled.

CASE EIGHT

A 52-year-old white male reported a lifelong history of premature ejaculation. At the time of consultation the patient was in a 15-year conflicted marital relationship. He ejaculated generally within 10 to 30 seconds of intromission, although he did not ejaculate quickly with either oral sex or stimulation by oo his wife. He had been tried on Prozac ® by another physician at a 40 mg. dosage level, but did poorly due to some side-effect profile and the fact that his premature ejaculation did not remain under control. He was begun on 20 mg. of Paxil ®, and evaluated at two week intervals. Both he and his wife noted that he was still ejaculating in less than 1 minute. He was then begun on 40 mg. of Paxil ®, and was able to sustain intercourse for approximately 2 minutes, but wished to last longer. This patient was then started on 60 mg. of Paxil ® and was able to last somewhere between 5 and 8 minutes on each and every sexual encounter.

The foregoing description and the accompanying case studies are presented as illustrative but are not to be construed as limiting the present invention. Still other variations within the spirit and scope of this invention are possible and will readily present themselves to those skilled in the art.

We claim:

1. A method of treating a male human patient suffering from premature ejaculation which comprises administering to the patient a dose of paroxetine effective to delay the onset of ejaculation by the patient during subsequent sexual intercourse.

2. The method in accordance with claim 1 wherein paroxetine is administered chronically and daily in an amount in the range of about 3 milligrams to about 30 milligrams per day.

3. The method in accordance with claim 1 wherein paroxetine is administered daily for a time period of at least about 3 months and in an amount in the range of about 3 milligrams to about 30 milligrams per day.

4. The method in accordance with claim 1 wherein paroxetine is administered daily for a time period of at least about 6 months and in an amount in the range of about 3 milligrams to about 30 milligrams per day.

5. The method in accordance with claim 1 wherein paroxetine is administered daily to the patient orally and as paroxetine hydrochloride in a pharmacologically suitable carrier.

6. The method in accordance with claim 1 wherein paroxetine is administered daily to the patient orally as paroxetine hydrochloride and according to the following schedule: (1) first a daily dose of about 10 to about 20 milligrams for a time period of about two weeks, (2) then a daily dose of about 20 to about 40 milligrams for a time period of about four weeks, (3) next a daily dose of about 20 to about 60 milligrams for a time period of about two weeks, and (4) thereafter a daily dose of about 20 to about 60 milligrams as a maintenance dose.

7. The method in accordance with claim 1 wherein paroxetine is administered as a paroxetine hydrochloride solution in an aqueous medium.

* * * * *